United States Patent [19]

Honda et al.

[11] Patent Number: 4,500,714
[45] Date of Patent: Feb. 19, 1985

[54] 3-SUBSTITUTED-UREIDO-N-PYRIDYL BENZAMIDES

[75] Inventors: Masamitsu Honda, Tokyo; Hideaki Nagai, Saitama; Shoko Takishima, Tokyo; Akinori Kawamura; Noriko Kawamura, both of Saitama; Takashi Dan, Tokyo; Masuo Koizumi, Tokyo; Yasushi Murakami, Tokyo; Yoshikazu Hinohara, Gunma; Hideki Nakano, Chiba; Yoshio Takagaki, Tokyo, all of Japan

[73] Assignee: Chugai Seiyaku Kabushiki Kaisha, Tokyo, Japan

[21] Appl. No.: 435,541

[22] Filed: Oct. 7, 1982

[30] Foreign Application Priority Data

Oct. 15, 1981 [JP] Japan ................................ 56-163495
Oct. 15, 1981 [JP] Japan ................................ 56-163496

[51] Int. Cl.$^3$ ............................................ C07D 213/75
[52] U.S. Cl. ..................................... 546/309; 546/337
[58] Field of Search ................. 546/309, 337; 424/263

[56] References Cited

U.S. PATENT DOCUMENTS

| 4,035,373 | 7/1977 | Roll ...................................... 546/233 |
| 4,044,147 | 8/1977 | Nelson ................................ 546/298 |
| 4,069,224 | 1/1978 | Callahan et al. ..................... 546/337 |
| 4,093,734 | 6/1978 | Krüger et al. ....................... 546/309 |

OTHER PUBLICATIONS

J. Med. Chem., 14 963–968 (1971).
J. Med. Chem., 13 280–284 (1970).

*Primary Examiner*—Jane T. Fan
*Attorney, Agent, or Firm*—Browdy and Neimark

[57] ABSTRACT

Benzamide derivatives of the formula:

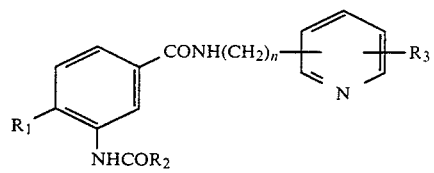

wherein $R_1$ is a hydrogen atom, a methyl group or a methoxy group; $R_2$ is a straight-chain or branched-chain alkyl group having 2 to 8 carbon atoms, a substituted phenyl group, or group —$NHR_4$, $R_4$ being a hydrogen atom, a straight-chain or branched-chain or cyclic alkyl group having 1 to 6 carbon atoms, or a phenyl group that may have a substituent on the nucleus; $R_3$ is a hydrogen atom or one or two alkyl groups having 1 to 4 carbon atoms and n is 0 or 1, a process for preparing these derivatives, and pharmaceutical compositions containing the same are provided.

The compounds of the above formula have the action to reduce the blood glucose level and, therefore, are useful as medicines.

8 Claims, No Drawings

3-SUBSTITUTED-UREIDO-N-PYRIDYL BENZAMIDES

The present invention relates to benzamide derivatives of the formula:

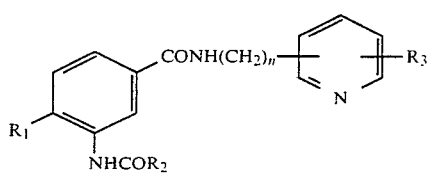
(I)

(wherein $R_1$ is a hydrogen atom, a methyl group or a methoxy group; $R_2$ is a straight-chain or branched-chain alkyl group having 2 to 8 carbon atoms, a substituted phenyl group, or group —$NHR_4$, $R_4$ being a hydrogen atom, a straight-chain or branched-chain or cyclic alkyl group having 1 to 6 carbon atoms, or a phenyl group that may have a substituent on the nucleus; $R_3$ is a hydrogen atom or one or two alkyl groups having 1 to 4 carbon atoms, and n is 0 or 1), a process for preparing these derivatives, and pharmaceutical compositions containing them. Examples of the substituent of the phenyl group of $R_2$ and $R_4$ in the formula (I) are a halogen atom, an alkyl group having 1 to 4 carbon atoms and an alkoxy group having 1 to 4 carbon atoms.

The compounds of the present invention that are represented by formula (I) are useful as medicines since they have the ability to reduce the blood glucose level.

One method of producing the compounds of the present invention comprises the steps of reacting 3-nitrobenzoyl chloride with amines in the presence of a base to form 3-nitrobenzamide derivatives and reducing them by a conventional technique to form 3-aminobenzamide derivatives, and reacting them with a carboxylic acid chloride or an isocyanate. This method is illustrated by the following reaction scheme wherein X is a halogen atom and the other symbols have the same meanings as defined above:

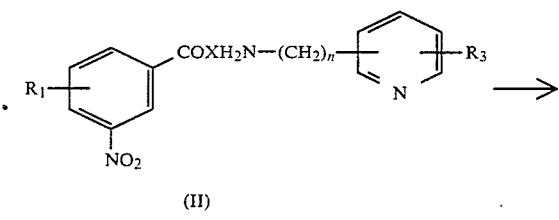
(II)

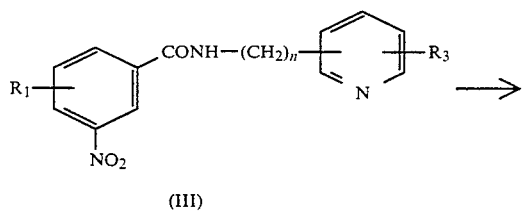
(III)

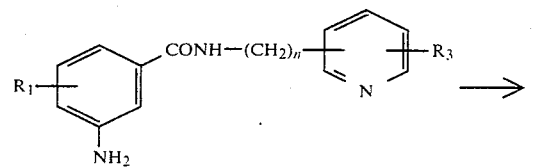
(IV)

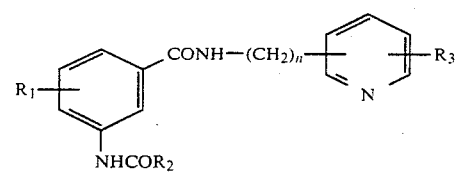
(I)

Compound (II) is reacted with aminopyridines under the conditions conventionally used for the reaction of forming acid amides; for example, the two compounds are reacted in a solvent such as acetone, tetrahydrofuran or dioxane, preferably in the presence of a base such as triethylamine or pyridine, at a temperature between 0° and 30° C. for a period of 1 to 5 hours.

Compound (III) can be readily converted to compound (IV) by catalytic reduction using a catalyst such as palladium-carbon, Raney's nickel or platinum dioxide.

Compound (IV) can be converted to the end compound (I) by reacting it with a reactive derivative of carboxylic acid or an isocyanate in the presence of a solvent such as tetrahydrofuran, dioxane, benzene or toluene, in the presence of a base such as triethylamine, pyridine dimethylanilin or picoline, at a temperature between 0° and 100° C. for a period of 1 to 48 hours.

The compound (I) so obtained is highly capable of reducing the blood glucose level and can be used as a medicine to treat diabetes.

The pharmaceutical composition containing the compound (I) of the present invention can be administered to human beings orally or parenterally by intramuscular, subcutaneous or intravenous injection or in the form of a suppository. The composition can be formulated in a suitable dosal form by any of the conventional drug-making techniques, and among the suitable drug forms are tablets, slow-release agents, powders, capsules, suspensions, injections and suppositories.

The present invention is now described in greater detail by reference to the following examples and experiments to which the scope of the invention is by no means limited.

EXAMPLE 1

To a mixture of 2-aminopyridine (28.2 g), triethylamine (45 ml) and acetone (600 ml), 3-nitrobenzoyl chloride (55.8 g) was gradually added with stirring under ice cooling. The mixture was stirred for 30 minutes under the same condition, then for one hour at room temperature. Thereafter, the reaction solution was poured into 3 liters of water, and the resulting crystal was collected by filtration, washed with water, and recrystallized from methanol to provide 58.5 g of 3-nitro-N-2-pyridylbenzamide as a colorless acicular crystal (yield: 80%, m.p. 156°–157° C.). Hydrogen was bubbled into a mixture of the 3-nitro-N-2-pyridylbenzamide (15.9 g), 10% palladium-carbon (1.5 g) and ethanol (300 ml). After a stoichiometric amount of hydrogen was absorbed, the catalyst was removed, the reaction mixture was concentrated under vacuum, and the residue was recrystallized from ethanol to provide 7.2 g of a colorless acicular crystal of 3-amino-N-2-pyridylbenzamide (yield: 52%, m.p. 113°–115° C.). To a mixture of the 3-amino-N-2-pyridylbenzamide (6.4 g), triethylamine (4.5 ml) and acetone (60 ml), propionic acid chloride (2.8 g) was gradually added with stirring at room temperature. After one hour of stirring, the reaction mixture was poured into 200 ml of water which was then made weakly alkaline by gradually adding a 10% solution of sodium hydroxide. The resulting crystal was collected by filtration, washed with water and recrystallized from methanol to provide 7.0 g of 3-propionyl-N-2-pyridyl-benzamide as a colorless acicular crystal (compound 1) (yield: 87%, m.p. 128°–129° C.).

Elemental analysis: Calculated for $C_{15}H_{15}N_3O_2$ (%): C, 66.90; H, 5.61; N, 15.61; Found (%): C, 66.97; H, 5.65; N, 15.52.

EXAMPLES 2–36

Compounds 2 to 36 having the characteristics shown in Table 1 below were prepared as in Example 1.

TABLE 1

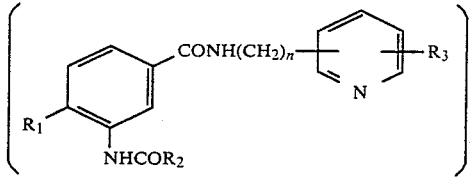

| No. | $R_1$ | $R_2$ | n | 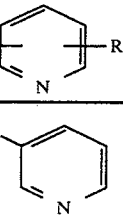 | molecular formula | m.p. (°C.) | yield (%) | elemental analysis C H N |
|---|---|---|---|---|---|---|---|---|
| 2 | H | $C_2H_5$ | 0 | 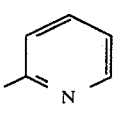 | $C_{15}H_{15}N_3O_2$ | 197–199 | 83 | cal'd (%) 66.90 5.61 15.61<br>found (%) 66.94 5.56 15.58 |
| 3 | " | " | 1 | 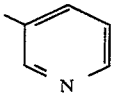 | $C_{16}H_{17}N_3O_2$ | 108–109 | 74 | cal'd (%) 67.82 6.05 14.83<br>found (%) 67.85 6.02 14.87 |
| 4 | " | " | 1 | 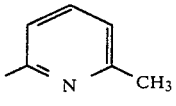 | " | 140–141 | 78 | cal'd (%) 67.82 6.05 14.83<br>found (%) 67.76 6.57 14.88 |
| 5 | " | " | 0 | 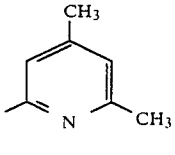 | " | 60–61 | 71 | cal'd (%) 67.82 6.05 14.83<br>found (%) 67.78 6.59 14.84 |
| 6 | " | " | 0 | 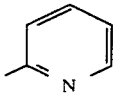 | $C_{17}H_{19}N_3O_2$ | 81–82 | 85 | cal'd (%) 68.66 6.44 14.13<br>found (%) 68.62 6.45 14.19 |
| 7 | " | n-$C_3H_7$ | 1 | 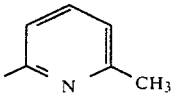 | " | 155–156 | 81 | cal'd (%) 68.66 6.44 14.13<br>found (%) 68.63 6.49 14.10 |
| 8 | " | " | 0 |  | " | 84–85 | 82 | cal'd (%) 68.66 6.44 14.13<br>found (%) 68.67 6.47 14.08 |
| 9 | " | i-$C_3H_7$ | 0 | " | " | 201–202 | 88 | cal'd (%) 68.66 6.44 14.13<br>found (%) 68.69 6.43 14.17 |

TABLE 1-continued $$\left\{\begin{array}{c}\text{CONH(CH}_2)_n\text{—pyridine—R}_3 \\ \text{R}_1 \quad \text{NHCOR}_2 \end{array}\right\}$$

| No. | R₁ | R₂ | n | pyridine-R₃ | molecular formula | m.p. (°C.) | yield (%) | elemental analysis C H N | | |
|---|---|---|---|---|---|---|---|---|---|---|
| 10 | " | n-C₄H₉ | 1 | 2-methylpyridine | C₁₈H₂₁N₃O₂ | 97–98 | 68 | cal'd (%) 69.43 6.80 13.50 found (%) 69.38 6.77 13.55 | | |
| 11 | " | " | 0 | 2,6-dimethylpyridine | " | 133–134 | 75 | cal'd (%) 69.43 6.80 13.50 found (%) 69.45 6.79 13.54 | | |
| 12 | " | i-C₄H₉ | 0 | " | " | 90–91 | 79 | cal'd (%) 69.43 6.80 13.50 found (%) 69.41 6.83 13.52 | | |
| 13 | " | n-C₅H₁₁ | 0 | " | C₁₉H₂₃N₃O₂ | 87–88 | 86 | cal'd (%) 70.13 7.12 12.91 found (%) 70.19 7.06 12.85 | | |
| 14 | " | n-C₆H₁₃ | 0 | " | C₂₀H₂₅N₃O₂ | 94–95 | 82 | cal'd (%) 70.77 7.43 12.38 found (%) 70.72 7.48 12.44 | | |
| 15 | " | n-C₇H₁₅ | 0 | " | C₂₁H₂₇N₃O₂ | 97–98 | 75 | cal'd (%) 71.36 7.70 11.89 found (%) 71.31 7.65 11.95 | | |
| 16 | " | n-C₈H₁₇ | 0 | 2,6-dimethylpyridine | C₂₂H₂₉N₃O₂ | 100–101 | 81 | cal'd (%) 71.90 7.95 11.44 found (%) 71.96 7.99 11.48 | | |
| 17 | " | p-tolyl | 0 | 3-pyridyl | C₂₀H₁₇N₃O₂ | 229–231 | 91 | cal'd (%) 72.49 5.17 12.68 found (%) 72.53 5.14 12.67 | | |
| 18 | " | " | 1 | " | C₂₁H₁₉N₃O₂ | 225–227 | 84 | cal'd (%) 73.02 5.55 12.17 found (%) 73.10 5.51 12.22 | | |
| 19 | " | " | 0 | 2-methylpyridine | " | 176–177 | 86 | cal'd (%) 73.02 5.55 12.17 found (%) 73.03 5.53 12.14 | | |
| 20 | " | p-methoxyphenyl | 0 | " | C₂₁H₁₉N₃O₃ | 183–185 | 80 | cal'd (%) 69.79 5.30 11.63 found (%) 69.84 5.33 11.67 | | |
| 21 | CH₃ | C₂H₅ | 1 | 2-pyridyl | C₁₇H₁₉N₃O₂ | 188–200 | 87 | cal'd (%) 68.66 6.44 14.13 found (%) 68.64 6.41 14.18 | | |
| 22 | " | " | 0 | 2,6-dimethylpyridine | " | 157–158 | 88 | cal'd (%) 68.66 6.44 14.13 found (%) 68.62 6.45 14.16 | | |

TABLE 1-continued $$\left\{ R_1 \underset{NHCOR_2}{\underset{|}{\bigotimes}} CONH(CH_2)_n \underset{N}{\bigotimes} R_3 \right\}$$

| No. | $R_1$ | $R_2$ | n | pyridine $R_3$ | molecular formula | m.p. (°C.) | yield (%) | elemental analysis C H N |
|---|---|---|---|---|---|---|---|---|
| 23 | " | n-$C_3H_7$ | 1 | 2-methylpyridine | $C_{18}H_{21}N_3O_2$ | 179–180 | 76 | cal'd (%) 69.43 6.80 13.50<br>found (%) 69.49 6.88 13.45 |
| 24 | " | " | 0 | 2,6-dimethylpyridine | " | 151–152 | 78 | cal'd (%) 69.43 6.80 13.50<br>found (%) 69.48 6.82 13.52 |
| 25 | " | i-$C_3H_7$ | 1 | 2-methylpyridine | " | 140–141 | 73 | cal'd (%) 69.43 6.80 13.50<br>found (%) 69.40 6.85 13.54 |
| 26 | " | " | 0 | 2,6-dimethylpyridine | " | 200–201 | 89 | cal'd (%) 69.43 6.80 13.50<br>found (%) 69.47 6.86 13.55 |
| 27 | " | n-$C_4H_9$ | 1 | 2-methylpyridine | $C_{19}H_{23}N_3O_2$ | 177–178 | 72 | cal'd (%) 70.13 7.12 12.91<br>found (%) 70.09 7.18 12.93 |
| 28 | " | " | 0 | 2,6-dimethylpyridine | " | 152–153 | 71 | cal'd (%) 70.13 7.12 12.91<br>found (%) 70.14 7.15 12.98 |
| 29 | $OCH_3$ | $C_2H_5$ | 1 | 3-methylpyridine | $C_{17}H_{19}N_3O_3$ | 86–87 | 74 | cal'd (%) 65.16 6.11 13.41<br>found (%) 65.19 6.14 13.37 |
| 30 | " | " | 0 | 2,6-dimethylpyridine | " | 142–143 | 78 | cal'd (%) 65.16 6.11 13.41<br>found (%) 65.18 6.08 13.44 |
| 31 | " | n-$C_3H_7$ | 1 | 3-methylpyridine | $C_{18}H_{21}N_3O_3$ | 139–140 | 76 | cal'd (%) 66.03 6.47 12.84<br>found (%) 66.06 6.42 12.81 |
| 32 | " | " | 0 | 2,6-dimethylpyridine | " | 77–78 | 84 | cal'd (%) 66.03 6.47 12.84<br>found (%) 66.01 6.41 12.89 |

TABLE 1-continued

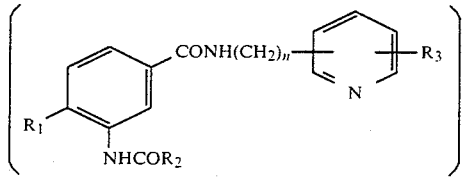

| No. | R₁ | R₂ | n | [pyridine with R₃] | molecular formula | m.p. (°C.) | yield (%) | elemental analysis C H N | | |
|---|---|---|---|---|---|---|---|---|---|---|
| 33 | " | i-C₃H₇ | 1 | 3-methylpyridine | " | 174–175 | 75 | cal'd (%) 66.03 6.47 12.84 found (%) 66.07 6.51 12.87 | | |
| 34 | " | " | 0 | 2,6-dimethylpyridine | " | 150–151 | 82 | cal'd (%) 66.03 6.47 12.84 found (%) 66.09 6.43 12.80 | | |
| 35 | " | n-C₄H₉ | 1 | 3-methylpyridine | C₁₉H₂₃N₃O₃ | 130–131 | 73 | cal'd (%) 66.84 6.79 12.31 found (%) 66.89 6.82 12.34 | | |
| 36 | " | " | 0 | 2,6-dimethylpyridine | " | 102–103 | 79 | cal'd (%) 66.84 6.79 12.31 found (%) 66.87 6.84 12.28 | | |

EXAMPLE 37

A mixture of the 3-amino-N-2-pyridylbenzamide (6.4 g), acetone (60 ml), methyl isocyanate (1.8 ml) and a catalytic amount of triethylamine were stirred at room temperature for 24 hours. The resulting crystal was collected by filtration and recrystallized from acetone to provide 6.9 g of 3-(3-methylureido)-N-2-pyridylbenzamide as a colorless acicular crystal (compound 37) (yield: 85%, m.p. 163°–164° C.).

Elemental analysis: Calculated for $C_{14}H_{14}N_4O_2$ (%): C, 62.21; H, 5.22; N, 20.73; Found (%): C, 62.18; H, 5.27; N, 20.78.

EXAMPLES 38–75

Compounds 38 to 75 having the characteristics shown in Table 2 below were prepared as in Example 37.

TABLE 2

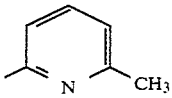

| No. | R₁ | R₂ | n | [pyridine with R₃] | molecular formula | m.p. (°C.) | yield (%) | elemental analysis C H N | | |
|---|---|---|---|---|---|---|---|---|---|---|
| 38 | H | —NHC₂H₅ | 0 | 2-methylpyridine | C₁₅H₁₆N₄O₂ | 154–155 | 81 | cal'd (%) 63.36 5.67 19.71 found (%) 63.39 5.62 19.78 | | |
| 39 | " | —NHn-C₃H₇ | 0 | " | C₁₆H₁₈N₄O₂ | 158–159 | 83 | cal'd (%) 64.41 6.08 18.78 found (%) 64.44 6.13 18.82 | | |
| 40 | " | —NHi-C₃H₇ | 0 | " | " | 173–174 | 88 | cal'd (%) 64.41 6.08 18.78 | | |

TABLE 2-continued $$\left( \begin{array}{c} \text{R}_1 \\ \end{array} \text{CONH(CH}_2)_n \begin{array}{c} \\ \text{N} \end{array} \text{R}_3 \right)$$

NHCOR₂

| No. | R₁ | R₂ | n | 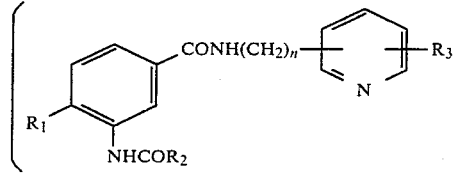 R₃ | molecular formula | m.p. (°C.) | yield (%) | | elemental analysis C H N | | |
|---|---|---|---|---|---|---|---|---|---|---|---|
| | | | | | | | | found (%) | 64.45 | 6.06 | 18.73 |
| 41 | " | 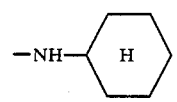 | 0 | " | C₁₉H₂₂N₄O₂ | 191–193 | 91 | cal'd (%) found (%) | 67.43 67.39 | 6.55 6.57 | 16.56 16.52 |
| 42 | " | —NHC₂H₅ | 0 | 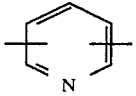 | C₁₅H₁₆N₄O₂ | 209–210 | 85 | cal'd (%) found (%) | 63.36 63.30 | 5.67 5.62 | 19.71 19.75 |
| 43 | " | —NHi-C₃H₇ | 1 | 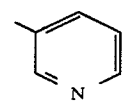 | C₁₇H₂₀N₄O₂ | 165–166 | 82 | cal'd (%) found (%) | 65.36 65.33 | 6.45 6.41 | 17.94 17.98 |
| 44 | " | —NHCH₃ | 0 | 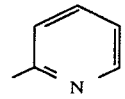 | C₁₅H₁₆N₄O₂ | 186–187 | 73 | cal'd (%) found (%) | 63.36 63.32 | 5.67 5.61 | 19.71 19.76 |
| 45 | " | —NHC₂H₅ | 0 | " | C₁₆H₁₈N₄O₂ | 185–186 | 79 | cal'd (%) found (%) | 64.41 64.37 | 6.08 6.06 | 18.78 18.72 |
| 46 | " | —NHn-C₃H₇ | 0 | " | C₁₇H₂₀N₄O₂ | 149–150 | 81 | cal'd (%) found (%) | 65.36 65.34 | 6.45 6.49 | 17.94 17.99 |
| 47 | " | —NHi-C₃H₇ | 0 | " | " | 183–184 | 80 | cal'd (%) found (%) | 65.36 65.31 | 6.45 6.42 | 17.94 17.98 |
| 48 | " | —NHn-C₄H₉ | 0 | " | C₁₈H₂₂N₄O₂ | 157–158 | 74 | cal'd (%) found (%) | 66.23 66.28 | 6.79 6.85 | 17.17 17.21 |
| 49 | " | 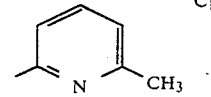 | 0 | " | C₂₀H₂₄N₄O₂ | 193–194 | 88 | cal'd (%) found (%) | 68.16 68.12 | 6.86 6.83 | 15.90 15.94 |
| 50 | " | 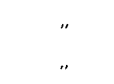 | 0 | " | C₂₀H₁₈N₄O₂ | 182–183 | 89 | cal'd (%) found (%) | 69.35 69.37 | 5.24 5.22 | 16.18 16.14 |
| 51 | " |  | 0 | " | C₂₀H₁₇ClN₄O₂ | 216–217 | 83 | cal'd (%) found (%) | 63.07 63.04 | 4.50 4.58 | 14.71 14.76 |
| 52 | " | —NHCH₃ | 0 |  | C₁₆H₁₈N₄O₂ | 139–140 | 76 | cal'd (%) found (%) | 64.41 64.36 | 6.08 6.05 | 18.78 18.74 |
| 53 | " | —NHC₂H₅ | 0 | " | C₁₇H₂₀N₄O₂ | 202–204 | 84 | cal'd (%) found (%) | 65.36 65.39 | 6.45 6.44 | 17.94 17.88 |
| 54 | " | —NHn-C₃H₇ | 0 | " | C₁₈H₂₂N₄O₂ | 192–193 | 82 | cal'd (%) found (%) | 66.23 66.27 | 6.79 6.72 | 17.17 17.24 |
| 55 | " | —NHi-C₃H₇ | 0 | " | " | 172–173 | 88 | cal'd (%) | 66.23 | 6.79 | 17.17 |

TABLE 2-continued $$\left( \underset{NHCOR_2}{\underset{R_1}{\bigotimes}} CONH(CH_2)_n \underset{N}{\bigotimes} R_3 \right)$$

| No. | R₁ | R₂ | n | ![pyridine with R₃] | molecular formula | m.p. (°C.) | yield (%) | | elemental analysis C H N |
|---|---|---|---|---|---|---|---|---|---|
| | | | | | | | | found (%) | 66.26 6.76 17.21 |
| 56 | " | —NH—⟨cyclohexyl H⟩ | 0 | " | C₂₁H₂₆N₄O₂ | 148–150 | 89 | cal'd (%)<br>found (%) | 68.83 7.15 15.29<br>68.87 7.17 15.24 |
| 57 | CH₃ | —NHCH₃ | 0 | ⟨3-pyridyl⟩ | C₁₅H₁₆N₄O₂ | 218–220 | 86 | cal'd (%)<br>found (%) | 63.36 5.67 19.71<br>63.31 5.62 19.76 |
| 58 | " | —NHC₂H₅ | 0 | " | C₁₆H₁₈N₄O₂ | 210–212 | 75 | cal'd (%)<br>found (%) | 64.41 6.08 18.78<br>64.48 6.06 18.73 |
| 59 | " | —NHn-C₃H₇ | 0 | " | C₁₇H₂₀N₄O₂ | 220–221 | 77 | cal'd (%)<br>found (%) | 65.36 6.45 17.94<br>65.33 6.42 17.99 |
| 60 | " | —NHi-C₃H₇ | 0 | " | " | 238–240 | 71 | cal'd (%)<br>found (%) | 65.36 6.45 17.94<br>65.30 6.41 17.98 |
| 61 | " | —NHCH₃ | 0 | ⟨2,6-dimethylpyridyl⟩ | C₁₆H₁₈N₄O₂ | 214–215 | 79 | cal'd (%)<br>found (%) | 64.41 6.08 18.78<br>64.48 6.03 18.75 |
| 62 | " | —NHC₂H₅ | 0 | " | C₁₇H₂₀N₄O₂ | 217–219 | 80 | cal'd (%)<br>found (%) | 65.36 6.45 17.94<br>65.34 6.48 17.97 |
| 63 | " | —NHn-C₃H₇ | 0 | " | C₁₈H₂₂N₄O₂ | 178–179 | 86 | cal'd (%)<br>found (%) | 66.23 6.79 17.17<br>66.27 6.75 17.12 |
| 64 | " | —NHi-C₃H₇ | 0 | " | " | 180–181 | 82 | cal'd (%)<br>found (%) | 66.23 6.79 17.17<br>66.28 6.79 17.18 |
| 65 | " | —NHn-C₄H₉ | 0 | " | C₁₉H₂₄N₄O₂ | 189–190 | 75 | cal'd (%)<br>found (%) | 67.03 7.11 16.46<br>67.07 7.18 16.42 |
| 66 | " | —NH—⟨cyclohexyl H⟩ | 0 | " | C₂₁H₂₆N₄O₂ | 192–193 | 92 | cal'd (%)<br>found (%) | 68.83 7.15 15.29<br>68.88 7.13 15.24 |
| 67 | " | —NH—⟨C₆H₄—Cl⟩ | 0 | " | C₂₁H₁₉ClN₄O₂ | 235–237 | 88 | cal'd (%)<br>found (%) | 63.87 4.85 14.19<br>63.84 4.89 14.25 |
| 68 | OCH₃ | —NHCH₃ | 0 | " | C₁₆H₁₈N₄O₃ | 203–204 | 75 | cal'd (%)<br>found (%) | 61.13 5.77 17.83<br>61.17 5.74 17.87 |
| 69 | " | —NHC₂H₅ | 0 | " | C₁₇H₂₀N₄O₃ | 165–166 | 72 | cal'd (%)<br>found (%) | 62.18 6.14 17.06<br>62.24 6.19 17.02 |
| 70 | " | —NHn-C₃H₇ | 0 | " | C₁₈H₂₂N₄O₃ | 164–165 | 80 | cal'd (%)<br>found (%) | 63.14 6.48 16.36<br>63.18 6.42 16.30 |
| 71 | " | —NHi-C₃H₇ | 0 | " | " | 144–145 | 88 | cal'd (%)<br>found (%) | 63.14 6.48 16.36<br>63.17 6.44 16.38 |
| 72 | " | —NHn-C₄H₉ | 0 | " | C₁₉H₂₄N₄O₃ | 147–148 | 76 | cal'd (%)<br>found (%) | 64.02 6.79 15.72<br>64.09 6.72 15.76 |
| 73 | " | —NH—⟨cyclohexyl H⟩ | 0 | " | C₂₁H₂₆N₄O₃ | 183–184 | 85 | cal'd (%)<br>found (%) | 65.95 6.85 14.65<br>65.91 6.89 14.63 |

TABLE 2-continued

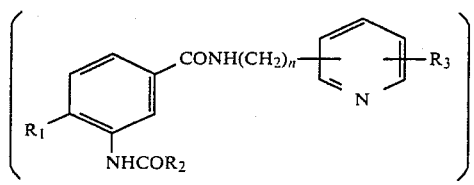
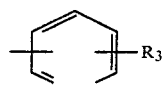

| No. | $R_1$ | $R_2$ | n |  | molecular formula | m.p. (°C.) | yield (%) | elemental analysis C H N | | |
|---|---|---|---|---|---|---|---|---|---|---|
| 74 | " | —NH—⌬—Cl | 0 | " | $C_{21}H_{19}ClN_4O_3$ | 191–192 | 82 | cal'd (%) found (%) | 61.39 4.66 61.32 4.60 | 13.64 13.59 |
| 75 | H | —$NH_2$ | 0 | " | $C_{14}H_{14}N_4O_2$ | 205–207 | 75 | cal'd (%) found (%) | 62.21 5.22 62.19 5.25 | 20.73 20.70 |

EXPERIMENTS

Groups each consisting of five male DDY mice (5 weeks old and weighing 25–30 g) were fasted 16 hours and given an intravenous injection of 75 mg/kg of alloxan. Forty-eight hours later, aqueous solutions or suspensions containing 200 mg/kg of the compounds indicated in Table 3 were orally administered to the mice, and 150 minutes later, blood was drawn from their hearts and the glucose level was measured by the glucose oxidase method. The results are shown in Table 3 and Table 4, wherein the compound numbers are keyed to those used in Examples 1 to 75.

TABLE 3

| Compound No. | blood glucose level (mg/dl) mean ± S.D. | Compound No. | blood glucose level (mg/dl) mean ± S.D. |
|---|---|---|---|
| none (control) | 485 ± 28 | 19 | 396 ± 29** |
| 1 | 389 ± 35** | 20 | 390 ± 25*** |
| 2 | 371 ± 29*** | 21 | 421 ± 38* |
| 3 | 392 ± 36** | 22 | 424 ± 34* |
| 4 | 403 ± 31** | 23 | 419 ± 27** |
| 5 | 368 ± 40*** | 24 | 405 ± 31** |
| 6 | 379 ± 33*** | 25 | 390 ± 29*** |
| 7 | 411 ± 29** | 26 | 378 ± 36*** |
| 8 | 415 ± 34** | 27 | 384 ± 28*** |
| 9 | 420 ± 25** | 28 | 391 ± 33** |
| 10 | 399 ± 19*** | 29 | 412 ± 38* |
| 11 | 385 ± 38** | 30 | 418 ± 25* |
| 12 | 392 ± 25*** | 31 | 390 ± 31*** |
| 13 | 393 ± 25*** | 32 | 385 ± 40** |
| 14 | 385 ± 31*** | 33 | 369 ± 29*** |
| 15 | 411 ± 28** | 34 | 396 ± 28** |
| 16 | 379 ± 33*** | 35 | 418 ± 33** |
| 17 | 407 ± 40** | 36 | 405 ± 29** |
| 18 | 405 ± 31** | | |

*$P < 0.05$
**$P < 0.01$
***$P < 0.001$

TABLE 4

| Compound No. | blood glucose level (mg/dl) mean ± S.D. | Compound No. | blood glucose level (mg/dl) mean ± S.D. |
|---|---|---|---|
| none (control) | 468 ± 31 | 56 | 388 ± 31** |
| | | 57 | 325 ± 29*** |
| 37 | 394 ± 28** | 58 | 415 ± 26* |
| 38 | 331 ± 41*** | 59 | 388 ± 32** |
| 39 | 368 ± 32** | 60 | 337 ± 24*** |
| 40 | 392 ± 33** | 61 | 369 ± 35** |
| 41 | 401 ± 27** | 62 | 386 ± 42** |
| 42 | 383 ± 31** | 63 | 363 ± 50** |
| 43 | 349 ± 25*** | 64 | 392 ± 37** |
| 44 | 377 ± 35** | 65 | 354 ± 36*** |
| 45 | 365 ± 28*** | 66 | 381 ± 29** |
| 46 | 351 ± 35*** | 67 | 399 ± 27** |
| 47 | 311 ± 30*** | 68 | 331 ± 29*** |
| 48 | 390 ± 29** | 69 | 362 ± 31*** |
| 49 | 403 ± 34* | 70 | 375 ± 34** |
| 50 | 411 ± 27* | 71 | 344 ± 36*** |
| 51 | 385 ± 40** | 72 | 366 ± 39** |
| 52 | 378 ± 21*** | 73 | 321 ± 36*** |
| 53 | 395 ± 33** | 74 | 347 ± 38*** |
| 54 | 342 ± 29*** | 75 | 341 ± 33*** |
| 55 | 365 ± 26*** | | |

*$P < 0.05$
**$P < 0.01$
***$P < 0.001$

What is claimed is:

1. A benzamide derivative of the formula:

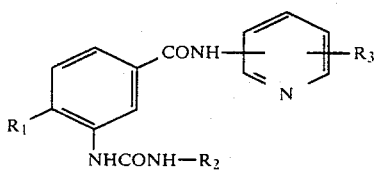

wherein $R_1$ is a hydrogen atom, a methyl group or a methoxy group; $R_2$ is a hydrogen atom, a straight-chain or branched-chain alkyl group having 1 to 6 carbon atoms or a cyclic alkyl group having 5 or 6 carbon atoms or an unsubstituted phenyl group or a phenyl group substituted with a halogen atom, an alkyl group having 1 to 4 carbon atoms or an alkoxy group having 1 to 4 carbon atoms on the nucleus; and $R_3$ is a hydrogen atom or one or two alkyl groups having 1 to 4 carbon atoms.

2. 3-(3-n-Propylureido)-N-(6-methyl-2-pyridyl)benzamide according to claim 1.

3. 3-(3-Isopropylureido)-N-(6-methyl-2-pyridyl)benzamide according to claim 1.

4. 3-(3-n-Butylureido)-N-(6-methyl-2-pyridyl)benzamide according to claim 1.

5. 3-(3-n-Butylureido)-4-methyl-N-(6-methyl-2-pyridyl)benzamide according to claim 1.

6. 3-(3-n-Butylureido)-4-methoxy-N-(6-methyl-2-pyridyl)benzamide according to claim 1.

7. 3-(3-Isopropylureido)-N-(4,6-dimethyl-2-pyridyl)benzamide according to claim 1.

8. 3-Ureido-N-(6-methyl-2-pyridyl)benzamide according to claim 1.

* * * * *